United States Patent
Fei et al.

(10) Patent No.: US 9,999,585 B2
(45) Date of Patent: Jun. 19, 2018

(54) PEROXIDE-STABLE ORAL CARE COMPOSITIONS

(71) Applicant: Colgate-Palmolive Company, New York, NY (US)

(72) Inventors: Lin Fei, Kendall Park, NJ (US); Prakasarao Mandadi, Flemington, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days. days.

(21) Appl. No.: 14/652,372

(22) PCT Filed: Dec. 14, 2012

(86) PCT No.: PCT/US2012/069896
§ 371 (c)(1),
(2) Date: Jun. 15, 2015

(87) PCT Pub. No.: WO2014/092737
PCT Pub. Date: Jun. 19, 2014

(65) Prior Publication Data
US 2015/0320665 A1   Nov. 12, 2015

(51) Int. Cl.
| A61Q 11/00 | (2006.01) |
| A61K 8/00 | (2006.01) |
| A61K 8/22 | (2006.01) |
| A61K 8/25 | (2006.01) |
| A61K 8/26 | (2006.01) |
| A61K 8/81 | (2006.01) |
| A61K 8/34 | (2006.01) |
| A61K 8/24 | (2006.01) |
| A61K 8/90 | (2006.01) |

(52) U.S. Cl.
CPC ............... *A61K 8/817* (2013.01); *A61K 8/22* (2013.01); *A61K 8/24* (2013.01); *A61K 8/25* (2013.01); *A61K 8/26* (2013.01); *A61K 8/345* (2013.01); *A61K 8/8176* (2013.01); *A61K 8/90* (2013.01); *A61Q 11/00* (2013.01)

(58) Field of Classification Search
USPC ..................................................... 424/49, 53
See application file for complete search history.

(56) References Cited

U.S. PATENT DOCUMENTS

| 5,776,435 A | 7/1998 | Gaffar et al. |
| 5,849,269 A | 12/1998 | Burgess et al. |
| 6,106,812 A | 8/2000 | Prencipe et al. |
| 6,110,446 A | 8/2000 | Prencipe et al. |
| 6,692,726 B1 | 2/2004 | Morgan et al. |
| 8,591,868 B2 | 11/2013 | Chopra et al. |
| 8,900,644 B2 | 12/2014 | Trivedi et al. |
| 2003/0152528 A1 | 8/2003 | Singh et al. |
| 2004/0109829 A1* | 6/2004 | Nonami ............... A61K 8/22 424/53 |
| 2005/0063923 A1 | 3/2005 | Prenicpe et al. |
| 2005/0163729 A1 | 7/2005 | Zaidel et al. |
| 2006/0062744 A1 | 3/2006 | Lokken |
| 2007/0003494 A1 | 1/2007 | Mori et al. |
| 2007/0071695 A1 | 3/2007 | Chopra et al. |
| 2010/0092407 A1 | 4/2010 | Kurata et al. |
| 2010/0119562 A1 | 5/2010 | Hilliard et al. |
| 2010/0322988 A1 | 12/2010 | Prencipe et al. |
| 2012/0058059 A1 | 3/2012 | Chopra et al. |
| 2012/0282192 A1 | 11/2012 | Miller et al. |
| 2012/0301522 A1 | 11/2012 | Prosise et al. |
| 2013/0287710 A1 | 10/2013 | Chopra et al. |

FOREIGN PATENT DOCUMENTS

| CN | 1816312 | 8/2006 |
| EP | 0839516 | 3/2003 |
| EP | 1504753 | 2/2005 |
| WO | WO 98/023248 | 6/1998 |
| WO | WO 07/123731 | 11/2007 |
| WO | WO 2011/079167 | * 6/2011 |
| WO | WO 12/102750 | 8/2012 |

OTHER PUBLICATIONS

International Search Report and Written Opinion in International Application No. PCT/US2012/069896, dated Oct. 10, 2013.
Rockwood Additives Ltd., 2002, "Laponitet® RD, D, G and XLG Safety Data Sheet," Rev. No. 03.
Written Opinion in Interntational Application No. pCT/US2012/069896, dated Jan. 19, 2015.
Corresponding Chinese Search Report and Office Action dated Jul. 27, 2016.
Blum et al., "Measurement of Clay Surface Areas by Polyvinylpyrolidone (PVP) Sorption and its Use for Quantifying Illite and Smectite Abundance", Clays and Clay Minerals, vol. 52, No. 5, pp. 589-602, 2004.

* cited by examiner

*Primary Examiner* — Lezah Roberts

(57) ABSTRACT

Described herein are oral care compositions comprising (i) a whitening complex comprising crosslinked polyvinylpyrrolidone complexed with hydrogen peroxide, and (ii) a hydrogen peroxide stabilizing agent comprising a clay comprising a lithium magnesium silicate or a sodium magnesium silicate, or a combination thereof.

30 Claims, No Drawings

PEROXIDE-STABLE ORAL CARE COMPOSITIONS

BACKGROUND

Dentifrice formulations comprising peroxide are known and useful for cleaning and whitening teeth. The peroxide can bleach the teeth, remove stains, and kill cariogenic bacteria. However, peroxide compounds are highly reactive, and consequently difficult to formulate. Moreover, hydrogen peroxide can spontaneously decompose to form oxygen gas ($O_2$) and water, so that on storage, the dentifrice containers may bloat, burst or leak, and the remaining formulation will not have enough peroxide remaining to clean and whiten teeth effectively. Some initially comprise very high levels of peroxide, which decomposes over time, so that the exact amount of peroxide delivered on application is variable and largely depends on how long and under what conditions the dentifrice has been stored.

However, known whitening dentifrice compositions including peroxide may exhibit an unacceptable level of peroxide decomposition and loss of whitening efficacy as a result of being stored prior to sale or by the user.

There is thus a need for improved peroxide-containing whitening oral care compositions, for example dentifrice compositions, which exhibit improved cosmetic stability of the peroxide, and so are chemically stable for long-term storage and are suitable for everyday consumer use without significant loss of whitening efficacy. Embodiments of the present invention at least partly aim to meet these needs.

SUMMARY

The invention also aims to provide a single phase whitening oral care composition, which not only exhibits cosmetic stability of the peroxide, and so is stable for long-term storage and is suitable for everyday consumer use, but also is more effective at whitening teeth using a bleaching mechanism.

Accordingly, the invention provides an oral care composition comprising (i) a whitening complex comprising crosslinked polyvinylpyrrolidone complexed with hydrogen peroxide, and (ii) a hydrogen peroxide stabilizing agent comprising a clay selected from a lithium magnesium silicate and a sodium magnesium silicate.

Optionally, the clay is a lithium magnesium silicate.
Optionally, the clay is a sodium magnesium silicate.
Optionally, the clay is a sodium lithium magnesium silicate.
Optionally, the clay is Laponite®, such as Laponite® XLG.
Optionally, the clay contains from 55 wt % to 65 wt % $SiO_2$, from 22 wt % to 32 wt % MgO, from 0.5 wt % to 1.5 wt % $Li_2O$, and from 2 wt % to 4 wt % $Na_2O$ based on a dry weight of the clay.

Optionally, the clay is present in an amount of from 0.1 wt % to 10 wt %, further optionally from 1 wt % to 5 wt %, further optionally from 1 wt % to 4 wt %, further optionally from 1 wt % to 3 wt %, further optionally from 1.5 wt % to 2.5 wt %, based on the weight of the composition.

Optionally, the composition comprises a polyvinylpyrrolidone thickening agent. Optionally, the polyvinylpyrrolidone thickening agent is present in an amount of from 1 wt % to 5 wt %, further optionally from 1 wt % to 4 wt %, further optionally from 1 wt % to 3 wt %, further optionally from 1.5 wt % to 2.5 wt %, based on the weight of the composition.

Optionally, the composition further comprises an ethylene oxide, propylene oxide block co-polymer of average molecular weight greater than 5000 Da, being substantially free of an ethylene oxide, propylene oxide block co-polymer of average molecular weight less than 5000 Da.

Further optionally, the ethylene oxide, propylene oxide block co-polymer comprises (ethylene oxide)$_x$-(propylene oxide)$_y$ wherein x is an integer of 80-150 and y is an integer 30-80.

Optionally, the ethylene oxide, propylene oxide block co-polymer is present in an amount of from 5 wt % to 10 wt % based on the weight of the composition.

Optionally, the crosslinked polyvinylpyrrolidone complexed with hydrogen peroxide is present in an amount of from 0.5 wt % to 20 wt %, further optionally from 6 wt % to 16 wt %, further optionally from 9 wt % to 13 wt %, further optionally from 10 wt % to 12 wt %, based on the weight of the composition.

Optionally, the whitening complex contains from 10 wt % to 30 wt % hydrogen peroxide and from 5 wt % to 15 wt % total nitrogen, based on the weight of the whitening complex.

Optionally, the total amount of hydrogen peroxide is from 0.5 wt % to 4 wt % based on the weight of the composition. Optionally, the total amount of hydrogen peroxide is from greater than 1.1 wt % to less than 3 wt % based on the weight of the composition. Optionally, the total amount of hydrogen peroxide is from 1.5 wt % to 2.5 wt % based on the weight of the composition.

Optionally, the composition further comprises an abrasive. Such abrasive may be selected from at least one of calcined alumina, silica, zirconium oxide, calcium pyrophosphate, dicalcium phosphate and precipitated calcium carbonate, or any mixture of two or more thereof.

Optionally, the abrasive is, or comprises, a calcium abrasive, such as calcium pyrophosphate.

Optionally, the abrasive is present in an amount of from 10 wt % to 20 wt %, further optionally from 13 wt % to 17 wt %, based on the weight of the composition.

Optionally, the composition further comprises at least one humectant selected from glycerin and propylene glycol, or a mixture thereof. Optionally, the at least one humectant is present in an amount of from 30 wt % to 70 wt %, further optionally from 40 wt % to 60 wt %, based on the weight of the composition. Optionally, the composition comprises propylene glycol in an amount of from 20 wt % to 40 wt %, further optionally from 25 wt % to 35 wt %, further optionally from 25 wt % to 30 wt %, based on the weight of the composition. Optionally, the composition comprises glycerin in an amount of from 15 wt % to 30 wt %, further optionally from 20 wt % to 30 wt %, further optionally from 20 wt % to 25 wt %, based on the weight of the composition.

Optionally, the composition further comprises polyethylene glycol of average molecular weight 400 to 800 Da. Optionally, the polyethylene glycol is present in an amount of from 1 wt % to 5 wt % based on the weight of the composition.

Optionally, the composition contains less than 3 wt % water based on the weight of the composition. Optionally, the composition is, or is substantially, anhydrous.

Optionally, the composition comprises the following ingredients by weight, each being based on the weight of the composition:

| | | |
|---|---|---|
| a. | Lithium magnesium silicate or sodium magnesium silicate | 1-4% |
| b. | Crosslinked polyvinylpyrrolidone | 1-4% |
| c. | Glycerin | 20-30% |
| d. | Propylene glycol | 20-35% |
| e. | Ethylene oxide, propylene oxide block co-polymer, avg. MW >5 kDa | 5-10% |
| f. | Polyethylene glycol 600 | 1-5% |
| g. | Crosslinked polyvinylpyrrolidone complexed with 15-25% $H_2O_2$ | 6-16% |
| h. | Calcium pyrophosphate | 10-20% |

Optionally, the composition is a single phase composition.

Optionally, the composition is a toothpaste.

In some embodiments, the composition further comprises an anionic surfactant in an amount of from 0.5 to 3 wt % based on the weight of the composition.

In the preferred embodiments of the invention, the oral care compositions exhibit cosmetic stability of the peroxide, and so are stable for long-term storage and are suitable for everyday consumer use, and also have great efficacy at whitening teeth using a bleaching mechanism.

Prior to the present invention, it was theorized that the inclusion of a clay to a formula comprising peroxide would increase the pH of the formula, and thus would destabilize the peroxide. Accordingly, it is considered that the skilled person would not have been motivated to consider adding a clay to such a formula.

However, the inventors have unexpectedly found that clay selected specifically from a lithium magnesium silicate and a sodium magnesium silicate, such as Laponite® XLG, remarkably increases peroxide stability in dentifrice. Accordingly, the level or concentration of peroxide in a dentifrice comprising such a specifically selected clay may be increased while maintaining stability of the peroxide, whereby the degree to which teeth may be whitened using the dentifrice may be increased.

The invention also provides a method of tooth whitening comprising applying the composition of the invention to the surface of a mammalian tooth.

Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

In some embodiments, the present invention provides an oral care composition comprising (i) a whitening complex comprising crosslinked polyvinylpyrrolidone complexed with hydrogen peroxide, and (ii) a hydrogen peroxide stabilizing agent comprising a clay selected from a lithium magnesium silicate and a sodium magnesium silicate.

The oral care composition typically is a single phase composition, for example a toothpaste.

In some embodiments, the present invention provides an oral care composition comprising (i) a peroxide source, and (ii) a hydrogen peroxide stabilizing agent comprising a clay selected from a lithium magnesium silicate and a sodium magnesium silicate. In some embodiments, the peroxide source is selected from hydrogen peroxide, sodium percarbonate, carbamide peroxide, crosslinked polyvinylpyrrolidone complexed with hydrogen peroxide, and combinations of two or more thereof.

In some embodiments, the peroxide source is present at a concentration effective to provide from about 0.1% to about 10% of hydrogen peroxide.

In some embodiments, the invention provides a toothpaste comprising an abrasive, e.g., a calcium abrasive. In other embodiments, the invention provides an abrasive-free gel.

In the oral care composition of the present invention, the whitening complex comprises crosslinked polyvinylpyrrolidone complexed with hydrogen peroxide.

In some embodiments, the crosslinked polyvinylpyrrolidone complexed with hydrogen peroxide is present in an amount of from 0.5 wt % to 20 wt % based on the weight of the composition.

In some embodiments, the crosslinked polyvinylpyrrolidone complexed with hydrogen peroxide is present in an amount of from 6 wt % to 16 wt % based on the weight of the composition.

In some embodiments, the crosslinked polyvinylpyrrolidone complexed with hydrogen peroxide is present in an amount of from 9 wt % to 13 wt % based on the weight of the composition.

In some embodiments, the crosslinked polyvinylpyrrolidone complexed with hydrogen peroxide is present in an amount of from 10 wt % to 12 wt % based on the weight of the composition.

Typically, the whitening complex contains from 10 wt % to 30 wt % hydrogen peroxide and from 5 wt % to 15 wt % total nitrogen, based on the weight of the whitening complex. Typically, the whitening complex contains from about 15% to about 25%, for example about 17% to about 22%, of hydrogen peroxide by weight, and about 7% to about 12% total nitrogen by weight.

In some embodiments, the total amount of hydrogen peroxide is from 0.5 wt % to 4 wt % based on the weight of the composition. In some embodiments, the total amount of hydrogen peroxide is greater than 1.1 wt % based on the weight of the composition. In some embodiments, the total amount of hydrogen peroxide is less than 3 wt % based on the weight of the composition. In some embodiments, the total amount of hydrogen peroxide is from 1.5 wt % to 2.5 wt % based on the weight of the composition. In some embodiments, the total amount of hydrogen peroxide is from 2 wt % to 2.5 wt % based on the weight of the composition.

In the oral care composition of the present invention, the hydrogen peroxide stabilizing agent comprises a clay selected from a lithium magnesium silicate and a sodium magnesium silicate.

In some embodiments, the clay is a lithium magnesium silicate. In some embodiments, the clay is a sodium magnesium silicate.

In some embodiments, the clay contains from 55 wt % to 65 wt % $SiO_2$, from 12 wt % to 30 wt % MgO, from 0.01 wt % to 1.5 wt % $Li_2O$, and from 2 wt % to 10 wt % $Na_2O$ based on a dry weight of the clay.

Typically, the clay is a sodium lithium magnesium silicate. In some embodiments, the clay is Laponite®, such as Laponite® XLG.

Laponite XLG has empirical formula: $Na^+_{0.7}[(Si_8Mg_{5.5}Li_{0.3})O_{20}(OH)_4]^{-0.7}$.

In some embodiments, the clay is present in an amount of from 0.1 wt % to 10 wt % based on the weight of the composition. In some embodiments, the clay is present in an amount of from 1 wt % to 5 wt % based on the weight of the composition. In some embodiments, the clay is present in an amount of from 1 wt % to 4 wt % based on the weight of the composition. In some embodiments, the clay is present in an amount of from 1 wt % to 3 wt % based on the weight of the composition. In some embodiments, the clay is present in an amount of from 1.5 wt % to 2.5 wt % based on the weight of the composition. In some embodiments, the clay is present in an amount of about 2 wt % based on the weight of the composition.

In some embodiments, the clay comprises particles having a d50 of about 25 nanometers. In some embodiments, the clay comprises particles having a thickness above about 1 nanometer.

In some embodiments, the composition comprises a thickening system. Typically, the thickening system comprises a polyvinvlpyrrolidone thickening agent.

In some embodiments, the polyvinvlpyrrolidone thickening agent is present in an amount of from 1 wt % to 5 wt % based on the weight of the composition. In some embodiments, the polyvinvlpyrrolidone thickening agent is present in an amount of from 1 wt % to 4 wt % based on the weight of the composition. In some embodiments, the polyvinvlpyrrolidone thickening agent is present in an amount of from 1 wt % to 3 wt % based on the weight of the composition. In some embodiments, the polyvinvlpyrrolidone thickening agent is present in an amount of from 1.5 wt % to 2.5 wt % based on the weight of the composition. In some embodiments, the polyvinvlpyrrolidone thickening agent is present in an amount of about 2 wt % based on the weight of the composition.

The compositions of the invention may optionally comprise an additional orally acceptable thickening agent, selected from one or more of, without limitation, carbomers, also known as carboxyvinyl polymers, carrageenans, also known as Irish moss and more particularly carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt % or about 1 wt % to about 5 wt %, based on the weight of the composition.

Some embodiments further comprise an abrasive. Yet further embodiments provide oral care compositions comprising from about 10 wt % to about 20 wt % abrasive, e.g. from about 13 wt % to about 17 wt %, based on the weight of the composition.

Where abrasives are present, the average particle size is typically about 0.1 to about 30 microns, for example about 1 to about 20 or about 5 to about 15 microns.

The abrasive is typically selected from at least one of calcined alumina, silica, zirconium oxide, calcium phosphate, calcium pyrophosphate, dicalcium phosphate dicalcium orthophosphate, tricalcium phosphate, calcium polymetaphosphate, and precipitated calcium carbonate, or any mixture of two or more thereof.

The abrasive may comprise a calcium abrasive, such as a calcium phosphate salt, e.g., calcium pyrophosphate, dicalcium orthophosphate dihydrate, tricalcium phosphate, and/or calcium polymetaphosphate. In a typical embodiment, the calcium abrasive comprises calcium pyrophosphate. In another embodiment, the calcium abrasive comprises calcium carbonate.

In some embodiments, the composition is a toothpaste comprising a calcium pyrophosphate abrasive. The calcium pyrophosphate may be present in an amount of from 10 wt % to 20 wt %, e.g. from 13 wt % to 17 wt %, based on the weight of the composition.

In some embodiments, the composition further comprises polymer thickeners selected from (i) polyethylene glycol, (ii) polyethylene glycol-polypropylene glycol block co-polymers having a molecular weight of at least 5000, and (iii) combinations thereof.

In some embodiments, the composition comprises an ethylene oxide, propylene oxide block co-polymer of formula (ethylene oxide)$_x$-(propylene oxide)$_y$, wherein x is an integer of 80-150, e.g. 100-130, e.g. about 116 or 118, and y is an integer of 30-80, e.g. about 60-70, e.g. about 66, having an average molecular weight of greater than 5000, e.g., 8000-13000 Da, e.g. about 9800;

In some embodiments, the composition comprises an ethylene oxide, propylene oxide block co-polymer of average molecular weight greater than 5000 Da, being substantially free of an ethylene oxide, propylene oxide block co-polymer of average molecular weight less than 5000 Da. The ethylene oxide, propylene oxide block co-polymer may be present in an amount of from 5 wt % to 10 wt % based on the weight of the composition. Block copolymers of ethylene oxide/propylene oxide are useful, but higher molecular weight, e.g., >5000 Da are preferred, e.g. including PLURACARE® L1220 (available from BASF, Wyandotte, Mich., United States of America).

In some embodiments, the composition further comprises polyethylene glycol of average molecular weight 400 to 800 Da, e.g., about 600 Da. Low or medium molecular weight polyethylene glycol, e.g., PEG 400, PEG 600, PEG 800, PEG 1000 and mixtures thereof are useful in the compositions of some embodiments of the invention.

The polyethylene glycol may be present in an amount of from 1 wt % to 5 wt % based on the weight of the composition. The polyethylene glycol may be present in an amount of from 2 wt % to 4 wt %, e.g. about 3 wt %, based on the weight of the composition.

In some embodiments, the oral care compositions may additionally comprise a stabilizing amount of an additional linear polyvinylpyrrolidone.

The compositions of the invention may also comprise various dentifrice ingredients to adjust the rheology and feel of the composition such as humectants, surface active agents, and/or gelling agents, etc.

In some embodiments, the oral care composition comprises a vehicle for the active components. The vehicle may comprise humectants, e.g. selected from glycerin, propylene glycol or a mixture or combination thereof.

In some embodiments, the oral care composition comprises from about 30 to about 70 wt %, such as from about 40 to about 60 wt %, humectant based on the weight of the composition.

In some embodiments, the composition comprises propylene glycol in an amount of from 20 wt % to 40 wt %, such as from 25 wt % to 35 wt % or from 25 wt % to 30 wt %, based on the weight of the composition.

In some embodiments, the composition comprises glycerin in an amount of from 15 wt % to 30 wt %, such as from 20 wt % to 30 wt % or from 20 wt % to 25 wt %, based on the weight of the composition.

Typical compositions of the invention have a "low water" content, meaning that a total concentration of water, including any free water and all water contained in any ingredients, is less than about 5 wt %, preferably less than 3 wt %, preferably less than 2 wt % water.

Optionally, the composition contains less than 3 wt % water based on the weight of the composition. In some embodiments, the oral care composition contains less than 2 wt % water, e.g., less than 1 wt % water, based on the weight of the composition. In some embodiments, the composition is substantially anhydrous.

It is preferred that the vehicle ingredients in particular provide a dentifrice with a viscosity of about 10,000 CPS to about 700,000 CPS, preferably about 30,000 CPS to about 300,000 CPS.

As recognized by one of skill in the art, the oral compositions of the invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine.

In some embodiments, the composition may additionally comprise an anionic surfactant, e.g., sodium lauryl sulfate (SLS). In some embodiments, the composition further comprises an anionic surfactant, such as SLS, in an amount of from 0.5 to 3 wt % based on the weight of the composition.

The compositions of the present invention optionally comprise one or more further active material(s), which is or are operable for the prevention or treatment of a condition or disorder of hard or soft tissue of the oral cavity, the prevention or treatment of a physiological disorder or condition, or to provide a cosmetic benefit.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition.

Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. Typically, the anticalculus agent is present at about 0.1% to about 30 wt % based on the weight of the composition.

The oral composition may include a mixture of different anticalculus agents.

In some embodiments, the composition additionally comprises a tartar control agent, e.g., selected from tetrasodium pyrophosphate (TSPP) and sodium tripolyphosphate (STPP). In some embodiments, the composition comprises TSPP in an amount of from 1 wt % to 3 wt % based on the weight of the composition.

In one preferred embodiment, tetrasodium pyrophosphate (TSPP) and sodium tripolyphosphate (STPP) are used. The anticalculus agent comprises TSPP at about 1-2% and STPP at about 7% to about 10%, each based on the weight of the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions, each based on the weight of the composition.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%, each based on the weight of the composition.

In some embodiments, the compositions of the invention optionally comprise an antimicrobial (e.g., antibacterial) agent, e.g., triclosan. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%, each based on the weight of the composition.

In some embodiments, the compositions of the invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the invention may optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

In some embodiments, the composition comprises the following ingredients by weight, each being based on the weight of the composition:

| | | |
|---|---|---|
| a. | Lithium magnesium silicate or sodium magnesium silicate | 1-4% |
| b. | Crosslinked polyvinylpyrrolidone | 1-4% |

-continued

| | | |
|---|---|---|
| c. | Glycerin | 20-30% |
| d. | Propylene glycol | 20-35% |
| e. | Ethylene oxide, propylene oxide block co-polymer, avg. MW >5 kDa | 5-10% |
| f. | Polyethylene glycol 600 | 1-5% |
| g. | Crosslinked polyvinylpyrrolidone complexed with 15-25% $H_2O_2$ | 6-16% |
| h. | Calcium pyrophosphate | 10-20% |

The compositions may optionally comprise any or all of the following ingredient classes and/or particular ingredients by weight, each being based on the weight of the composition:

| | |
|---|---|
| Humectants, 35-60%, e.g. | |
| Glycerin | 15-30%, e.g., about 20-25% |
| Propylene glycol | 20-35%, e.g., about 25-30% |
| Hydrogen peroxide stabilizing agent, 1-5%, e.g. | |
| Laponite ® XLG | 1-5%, e.g., about 1.5-3% |
| Thickeners, e.g. | |
| Crosslinked polyvinylpyrrolidone | 1-5%, e.g., about 1.5-3% |
| Polymers 10-25%, e.g., | |
| Ethylene oxide, propylene oxide block co-polymer, avg. MW >5 kDa | 5-10%, e.g., about 6-8% |
| Polyethylene glycol 600 | 1-5%, e.g., about 3% |
| Whitener, 5-20%, e.g., | |
| Crosslinked polyvinylpyrrolidone complexed with 15-25% hydrogen peroxide | 5-20%, e.g., about 9-13% |
| Abrasive, 5-25%, e.g. | |
| Calcium pyrophosphate | 10-20%, e.g., about 13-17% |
| Fluoride, 0-1%, e.g. | |
| Sodium monofluorophosphate | 0.5-1%, e.g., about 0.76% |
| Surfactant, e.g., SLS | 0-3%, e.g., about 2% |
| Tartar control agent, e.g. TSPP | 0.5-5%, e.g., about 2% |
| Antioxidant, 0.01-5%, e.g. BHT | about 0.03% |
| Flavorings | 0.1-5% |
| Water | <3% |

Methods are provided to whiten an oral surface in a human or animal subject comprising storing in stable form a composition of the invention, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with particular embodiments of the invention, is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The invention is illustrated in the following non-limiting examples.

EXAMPLES

Comparative Examples 1 to 5

Dentifrice compositions, not according to the present invention, are prepared according to Comparative Examples 1 to 5. The compositions have the following ingredients as specified in Table 1, in which the amounts are in wt %:

TABLE 1

| Ingredient | Comp. Ex. 1 | Comp. Ex. 2 | Comp. Ex. 3 | Comp. Ex. 4 | Comp. Ex. 5 |
|---|---|---|---|---|---|
| 85 wt % syrupy phosphoric acid | 0.2 | 0.2 | 0.2 | 0.2 | 0.2 |
| PEG 600 | 3 | 3 | 3 | 3 | 3 |
| $PEG_{116}/PPG_{66}$ co-polymer (Pluracare L1220F) | 7.5 | 7.5 | 7.5 | 7.5 | 7.5 |
| Glycerin | 23.61 | 23.61 | 23.61 | 23.61 | 23.61 |
| Propylene glycol | 30 | 28 | 28 | 28 | 28 |
| Bentonite | — | 2 | 2 | — | — |
| Montmorillonite | — | — | — | 2 | — |
| Kaolinite | — | — | — | — | 2 |
| Crosslinked PVP | 2 | 2 | 2 | 2 | 2 |
| Crosslinked $PVP/H_2O_2$ complex | 11 | 11 | 11 | 11 | 11 |
| Sodium saccharin | 0.6 | 0.6 | 0.6 | 0.6 | 0.6 |
| Sucralose | 0.05 | 0.05 | 0.05 | 0.05 | 0.05 |
| Sodium monofluorophosphate | 0.76 | 0.76 | 0.76 | 0.76 | 0.76 |
| Tetrasodium pyrophosphate (TSPP) | 2 | 2 | 2 | 2 | 2 |
| Butylated hydroxytoluene (BHT) | 0.03 | 0.03 | 0.03 | 0.03 | 0.03 |
| Flavor | 2.25 | 2.25 | 2.25 | 2.25 | 2.25 |
| Sodium lauryl sulfate (SLS) | 2 | 2 | 2 | 2 | 2 |
| Calcium pyrophosphate | 15 | 15 | 15 | 15 | 15 |
| Total | 100 | 100 | 100 | 100 | 100 |

The dentifrice of Comparative Example 1 comprised a whitening complex comprising a complex of crosslinked polyvinvlpyrrolidone and hydrogen peroxide. The hydrogen peroxide comprised approximately 2 wt % of the total weight of the dentifrice. The dentifrice comprised a substantially anhydrous vehicle comprising $PEG_{116}/PPG_{66}$ co-polymer (Pluracare L1220F), glycerin, propylene glycol and PEG 600.

Each of the dentifrice compositions of Comparative Examples 2 to 5 comprised a clay in place of some of the propylene glycol of Comparative Example 1.

More specifically, the dentifrice compositions of Comparative Examples 2 and 3 comprised the same composition as the dentifrice of Comparative Example 1, except that in Comparative Examples 2 and 3 the compositions comprised 2 wt % bentonite and 28 wt % propylene glycol, whereas Comparative Example 1 had no bentonite and had 30 wt % propylene glycol. The dentifrice of Comparative Example 4 comprised the same composition as the dentifrice of Comparative Example 1, except that in Comparative Example 4 the composition comprised 2 wt % montmorillonite and 28 wt % propylene glycol, whereas Comparative Example 1 had no montmorillonite and had 30 wt % propylene glycol. The dentifrice of Comparative Example 5 comprised the same composition as the dentifrice of Comparative Example 1, except that in Comparative Example 5 the composition comprised 2 wt % kaolinite and 28 wt % propylene glycol, whereas Comparative Example 1 had no kaolinite and had 30 wt % propylene glycol.

The stability of the hydrogen peroxide in the respective dentifrices of Comparative Examples 1 to 5 was evaluated using a testing protocol that evaluated the chemical stability of the hydrogen peroxide in the dentifrices.

Hydrogen peroxide chemically decomposes into the decomposition products of water and oxygen gas, with two moles of hydrogen peroxide producing one mole of oxygen. However, one mole of oxygen gas takes up more volume than two moles of hydrogen peroxide, and so significant pressure can build up in a closed tube of dentifrice as hydrogen peroxide chemically degrades.

In each of Comparative Examples 1 to 5, while at room temperature, respective identical conventional flexible polymer four ounce (4 oz.) toothpaste tubes were filled with about 95 grams of the respective dentifrice compositions and the tubes were closed with respective conventional closures. For each tube used in Comparative Examples 1 to 5, the perimeter of a portion (herein called the "tube waist") of the tube approximately midway between its two longitudinal ends and the perimeter of a portion (herein called the "tube end") of the tube adjacent its closure end were measured and recorded on the day of filling the tube, while the tube still was at room temperature.

Bloating of the hydrogen peroxide-containing dentifrice formulae of Comparative Examples 1 to 5 resulting from the decomposition of the hydrogen peroxide was measured by re-measuring the respective tube waists and tube ends after seven days of 60° C. accelerated aging of the tube. As the tubes swell due to internal pressure exerted by oxygen gas, the perimeters of the tubes at their tube waist and tube end correspondingly increase.

Table 2 shows the increase in the perimeter of the tubes at their respective tube waists and tube ends as a function of time at 60° C. for the dentifrice compositions of Comparative Examples 1 to 5.

TABLE 2

| | | Comp. Ex. 1 | Comp. Ex. 2 | Comp. Ex. 3 | Comp. Ex. 4 | Comp. Ex. 5 |
|---|---|---|---|---|---|---|
| Room temp. sample | Tube waist perimeter (cm) | 11.1 | 11.1 | 11.1 | 11.1 | 11.1 |
| | Tube end perimeter (cm) | 11.1 | 11.1 | 11.1 | 11.1 | 11.1 |
| Aged sample | Tube waist perimeter (cm) | 11.6 | Burst | Burst | Burst | 12.2 |
| | Tube end perimeter (cm) | 11.6 | Burst | Burst | Burst | 12.2 |
| Change | Tube waist perimeter (cm) | 0.5 | N/A | N/A | N/A | 1.1 |
| | Tube end perimeter (cm) | 0.5 | N/A | N/A | N/A | 1.1 |

It may be seen that, in Comparative Example 1, there was significant increase in the perimeter of the tube at the tube waist and in the perimeter of the tube at the tube end, indicating that there was significant hydrogen peroxide decomposition over the course of the accelerated aging test.

Moreover, it may be seen that, during the accelerated aging test, the tubes of Comparative Examples 2 to 5 bloated to such an extent that they burst, leaving the tube waist and tube end perimeters of the tubes of Comparative Examples 2 to 5 immeasurable after the accelerated aging test ("Change" designated as "N/A" in Table 2 for tubes that burst). This indicates that there was significant hydrogen peroxide decomposition over the course of the accelerated aging tests, and likely a greater amount of hydrogen peroxide decomposition over the course of the accelerated aging tests than during the accelerated aging test of Comparative Example 1.

Evidently, the hydrogen peroxide had poor chemical stability in the accelerated aging tests of each of Comparative Examples 1 to 5. Further, the inclusion of one of the clays, bentonite, montmorillonite and kaolinite, appears to have worsened the chemical stability of the hydrogen peroxide. These results support the theory prior to the present invention that inclusion of a clay to a formula comprising peroxide would increase the pH of the formula, and thus would destabilize the peroxide.

Example 1

A dentifrice according to the present invention was prepared according to Example 1. The composition had the following ingredients as specified in Table 3, in which the amounts are in wt %:

TABLE 3

| Ingredient | Example 1 |
|---|---|
| 85 wt % syrupy phosphoric acid | 0.2 |
| PEG 600 | 3 |
| $PEG_{116}/PPG_{66}$ co-polymer (Pluracare L1220F) | 7.5 |
| Glycerin | 23.61 |
| Propylene glycol | 28 |
| Sodium lithium magnesium silicate | 2 |
| Crosslinked PVP | 2 |
| Crosslinked $PVP/H_2O_2$ complex | 11 |
| Sodium saccharin | 0.6 |
| Sucralose | 0.05 |
| Sodium monofluorophosphate | 0.76 |
| Tetrasodium pyrophosphate (TSPP) | 2 |
| Butylated hydroxytoluene (BHT) | 0.03 |
| Flavor | 2.25 |
| Sodium lauryl sulfate (SLS) | 2 |
| Calcium pyrophosphate | 15 |
| Total | 100 |

The dentifrice of Example 1 comprised the same composition as the dentifrice of Comparative Example 1, except that in Example 1 the composition comprised 2 wt % of a clay comprising a sodium lithium magnesium silicate and 28 wt % propylene glycol, whereas Comparative Example 1 did not contain a sodium lithium magnesium silicate and had 30 wt % propylene glycol.

The stability of the hydrogen peroxide in the dentifrice of Example 1 was evaluated using the same testing protocol as described above for Comparative Examples 1 to 5. The same type of conventional flexible polymer four ounce (4 oz.) toothpaste tube was filled with the same volume (about 95 grams) of the dentifrice of Example 1 and the tube was closed with a conventional closure. Again, the perimeters of the tube waist and of the tube end were measured and recorded on the day of filling the tube, while the tube still was at room temperature, and were re-measured after seven days of 60° C. accelerated aging of the tube.

Table 4 shows the perimeter of the tube at its tube waist and tube end as a function of time at 60° C. for the dentifrice of Example 1.

TABLE 4

|  | Perimeter (cm) | Example 1 |
|---|---|---|
| Room temp. sample | Tube waist | 11.1 |
|  | Tube end | 11.1 |
| Aged sample | Tube waist | 11.1 |
|  | Tube end | 11.1 |
| Change | Tube waist | 0 |
|  | Tube end | 0 |

Table 4 shows that, as a function of time at 60° C., for the dentifrice of Example 1, there was no change in the perimeter of the tube at the tube waist or at the tube end. That is, for the dentifrice of Example 1, surprisingly there was no sign of bloating.

It may be seen from a comparison of the resultant data from Example 1 and Comparative Examples 1 to 5 that the inclusion of a clay comprising a sodium lithium magnesium silicate in the dentifrice of Example 1 significantly, and remarkably, reduced decomposition of hydrogen peroxide in the dentifrice composition, thereby significantly enhancing the chemical stability of the dentifrice.

In summary, the data described in the Examples evidences the unexpected improvement in the chemical stability of a dentifrice comprising a whitening complex comprising crosslinked polyvinylpyrrolidone complexed with hydrogen peroxide and a hydrogen peroxide stabilizing agent comprising a clay comprising a sodium lithium magnesium silicate, in accordance with the invention.

While particular embodiments of the invention have been illustrated and described, it will be obvious to those skilled in the art that various changes and modifications may be made without departing from the scope of the invention as defined in the appended claims.

What is claimed is:

1. An oral care composition comprising (i) a whitening complex comprising crosslinked polyvinylpyrrolidone complexed with hydrogen peroxide, and (ii) a hydrogen peroxide stabilizing agent comprising a clay comprising a sodium lithium magnesium silicate, wherein the clay is present in an amount of from 0.5 wt % to 5 wt % based on the weight of the composition, and wherein the clay comprises from 55 wt % to 65 wt % $SiO_2$, from 22 wt % to 32 wt % MgO, from 0.5 wt % to 1.5 wt % $Li_2O$, and from 2 wt % to 4 wt % $Na_2O$ based on a dry weight of the clay.

2. The composition of claim 1 wherein the clay is present in an amount of from 1 wt % to 3 wt % based on the weight of the composition.

3. The composition of claim 1 further comprising a polyvinvlpyrrolidone thickening agent.

4. The composition of claim 3 wherein the polyvinvlpyrrolidone thickening agent is present in an amount of from 1 wt % to 5 wt % based on the weight of the composition.

5. The composition of claim 1 further comprising an ethylene oxide, propylene oxide block co-polymer of average molecular weight greater than 5000 Da, being substantially free of an ethylene oxide, propylene oxide block co-polymer of average molecular weight less than 5000 Da.

6. The composition of claim 5 wherein the ethylene oxide, propylene oxide block co-polymer comprises (ethylene oxide)$_x$-(propylene oxide)$_y$, wherein x is an integer of 80-150 and y is an integer of 30-80.

7. The composition of claim 5 wherein the ethylene oxide, propylene oxide block co-polymer is present in an amount of from 5 wt % to 10 wt % based on the weight of the composition.

8. The composition of claim 1 wherein the crosslinked polyvinylpyrrolidone complexed with hydrogen peroxide is present in an amount of from 0.5 wt % to 20 wt % based on the weight of the composition.

9. The composition of claim 8 wherein the crosslinked polyvinylpyrrolidone complexed with hydrogen peroxide is present in an amount of from 6 wt % to 16 wt % based on the weight of the composition.

10. The composition of claim 6 wherein the crosslinked polyvinylpyrrolidone complexed with hydrogen peroxide is present in an amount of from 9 wt % to 13 wt % based on the weight of the composition.

11. The composition of claim 1 wherein the whitening complex contains from 10 wt % to 30 wt % hydrogen peroxide and from 5 wt % to 15 wt % total nitrogen, based on the weight of the whitening complex.

12. The composition of claim 1 wherein the total amount of hydrogen peroxide is from 0.1 wt % to 4 wt % based on the weight of the composition.

13. The composition of claim 12 wherein the total amount of hydrogen peroxide is from greater than 0.5 wt % to less than 3 wt % based on the weight of the composition.

14. The composition of claim 1 further comprising an abrasive.

15. The composition of claim 14 wherein the abrasive is selected from at least one of calcined alumina, silica, zirconium oxide, calcium pyrophosphate, dicalcium phosphate and precipitated calcium carbonate, or any mixture of two or more thereof.

16. The composition of claim 14 wherein the abrasive is a calcium abrasive.

17. The composition of claim 16 wherein the abrasive is a calcium pyrophosphate.

18. The composition of claim 14 wherein the abrasive is present in an amount of from 10 wt % to 20 wt % based on the weight of the composition.

19. The composition of claim 1 further comprising at least one humectant selected from glycerin and propylene glycol, or a mixture thereof.

20. The composition of claim 19 wherein the at least one humectant is present in an amount of from 30 wt % to 70 wt % based on the weight of the composition.

21. The composition of claim 20 wherein the at least one humectant is present in an amount of from 40 wt % to 60 wt % based on the weight of the composition.

22. The composition of claim 19 comprising propylene glycol in an amount of from 20 wt % to 40 wt % based on the weight of the composition.

23. The composition of claim 19 comprising glycerin in an amount of from 15 wt % to 30 wt % based on the weight of the composition.

24. The composition of claim 1 further comprising polyethylene glycol of average molecular weight 400 to 800 Da.

25. The composition of claim 24 wherein the polyethylene glycol is present in an amount of from 1 wt % to 5 wt % based on the weight of the composition.

26. The composition of claim 1 which contains less than 3 wt % water based on the weight of the composition.

27. The composition of claim 1 comprising the following ingredients by weight, each being based on the weight of the composition:

| a. | Sodium lithium magnesium silicate | 1-4% |
|---|---|---|
| b. | Crosslinked polyvinylpyrrolidone | 1-4% |
| c. | Glycerin | 20-30% |

-continued

| | | |
|---|---|---|
| d. | Propylene glycol | 20-35% |
| e. | Ethylene oxide, propylene oxide block co-polymer, avg. MW >5 kDa | 5-10% |
| f. | Polyethylene glycol 600 | 1-5% |
| g. | Crosslinked polyvinylpyrrolidone complexed with 15-25% $H_2O_2$ | 0.5-16.5% |
| h. | Calcium pyrophosphate | 10-20%. |

28. The composition of claim 1 which is a single phase composition.

29. The composition of claim 1 which is a toothpaste.

30. A method of tooth whitening comprising applying the composition of claim 1 to the surface of a mammalian tooth.

\* \* \* \* \*